United States Patent
Chalupper

(10) Patent No.: US 8,929,576 B2
(45) Date of Patent: Jan. 6, 2015

(54) METHOD FOR TUNING A HEARING DEVICE USING A PERCENTILE ANALYSIS, AND TUNING DEVICE

(75) Inventor: Josef Chalupper, Paunzhausen (DE)

(73) Assignee: Siemens Medical Instruments Pte. Ltd., Singapore (SG)

( * ) Notice: Subject to any disclaimer, the term of this patent is extended or adjusted under 35 U.S.C. 154(b) by 0 days.

(21) Appl. No.: 13/877,237

(22) PCT Filed: Sep. 28, 2011

(86) PCT No.: PCT/EP2011/066863
§ 371 (c)(1),
(2), (4) Date: Apr. 26, 2013

(87) PCT Pub. No.: WO2012/041904
PCT Pub. Date: Apr. 5, 2012

(65) Prior Publication Data
US 2013/0208934 A1 Aug. 15, 2013

(30) Foreign Application Priority Data
Sep. 30, 2010 (DE) .......................... 10 2010 041 775

(51) Int. Cl.
*H04R 25/00* (2006.01)
*A61B 5/12* (2006.01)

(52) U.S. Cl.
CPC ................ *H04R 25/30* (2013.01); *A61B 5/121* (2013.01); *H04R 25/70* (2013.01)
USPC ........... 381/314; 381/321; 381/316; 381/312; 381/60

(58) Field of Classification Search
CPC ...... H04R 25/30; H04R 25/70; H04R 25/502; H04R 25/505; H04R 25/305; H04R 2225/41; H04R 25/554; H04R 25/356; H04R 25/558; H04R 25/353; H04R 2225/43; H04R 2430/03; H04R 25/40; H04R 29/00; H04R 25/35; H04R 25/50; H04R 25/55; H04R 25/556; H04R 2225/81; H04R 2225/83; H04R 2225/39; G10L 21/00; A61B 5/121
USPC ............................ 381/60, 312, 314, 316, 321
See application file for complete search history.

(56) References Cited

U.S. PATENT DOCUMENTS

| | | | |
|---|---|---|---|
| 4,577,641 A * | 3/1986 | Hochmair et al. ............ | 600/559 |
| 4,953,112 A * | 8/1990 | Widin et al. ...................... | 703/6 |
| 2008/0298600 A1 * | 12/2008 | Poe et al. .......................... | 381/60 |
| 2009/0028351 A1 | 1/2009 | Andersen | |

FOREIGN PATENT DOCUMENTS

| | | |
|---|---|---|
| EP | 0396831 A2 | 11/1990 |
| WO | 2007112737 A1 | 10/2007 |

OTHER PUBLICATIONS

Dynamic REM with Percentile Analysis, Otometrics.com, Retrieved from the internet on Mar. 6, 2014: http://www.otometrics.com/18/media/D437BCDA72D0437D94882C4D2640D5D3.ashx.*

(Continued)

*Primary Examiner* — Ahmad F. Matar
*Assistant Examiner* — Sabrina Diaz
(74) *Attorney, Agent, or Firm* — Laurence A. Greenberg; Werner H. Stemer; Ralph E. Locher

(57) ABSTRACT

High-quality adjustment of a hearing apparatus, and in particular of a hearing aid, is accelerated. In the adjusting method, a percentile analysis is carried out in order to obtain at least one frequency response of the hearing apparatus. Any discrepancy between the frequency response and an intended gain characteristic is determined. The setting of the hearing apparatus is then changed, such that the discrepancy is reduced. In order to check the effect of the setting change, a current frequency response after variation of the setting is determined by providing a constant noise signal or a single sinusoidal sweep at the input of the hearing apparatus and level measurement at the output. This frequency response measurement can be carried out as a second step considerably more quickly than the very precise percentile analysis at the start of the process.

11 Claims, 3 Drawing Sheets

(56) References Cited

OTHER PUBLICATIONS

Jens Ulrich et al.,: "Hoehrakustik Theorie Und Praxis", 1. Edition; Heidelberg, Germany; DOZ, 2007, pp. 880-881, 914-918, 1015-1018; ISBN 978-3-922269-80-9—English translation.

Matthias Parr: "Messen Von Hoehrsystem-Funktionselementen"; Internet; Mar. 31, 1999; URL:http://acousticon.eu/start/index.php?option=com_docman&task=doc_download&gid=83 English abstract.

* cited by examiner

METHOD FOR TUNING A HEARING DEVICE USING A PERCENTILE ANALYSIS, AND TUNING DEVICE

BACKGROUND OF THE INVENTION

Field of the Invention

The present invention relates to a method for tuning a hearing device. In addition to this the present invention relates to a corresponding tuning device. Here, the term hearing device is to be understood as any sound-emitting device which can be worn in or on the ear, in particular a hearing aid, a headset, earphone and the like.

Hearing aids are hearing devices which can be worn and which serve to assist the hard-of-hearing. In order to meet the numerous individual needs, different forms of construction of hearing aids are provided, such as behind-the-ear (BTE) hearing aids, hearing aids with an external microphone (RIC: receiver in the canal) and in-the-ear (ITE) hearing aids, including for example conch hearing aids or canal hearing aids (ITE, CIC). The hearing aids listed by way of example are worn on the outer ear or in the auditory canal. In addition however bone-conduction, implantable or vibrotactile hearing aids are also available on the market. With these, stimulation of the damaged hearing is either mechanical or electrical.

In principle, hearing aids have as their essential components an input transducer, an amplifier and an output transducer. In general, the input transducer is a sound receiver, e.g. a microphone, and/or an electromagnetic receiver, e.g. an induction coil. The output transducer is mostly realized as an electro-acoustic transducer, e.g. a miniature loudspeaker, or as an electro-mechanical transducer, e.g. a bone conduction earpiece. The amplifier is commonly integrated into a signal processing unit. This structural principle is illustrated in FIG. 1 by the example of a behind-the-ear hearing aid. Built into a hearing aid housing 1 which is to be worn behind the ear are one or more microphones 2 for the purpose of receiving sound from the surroundings. A signal processing unit 3, which is also integrated into the hearing aid housing 1, processes the microphone signals and amplifies them. The output signal from the signal processing unit 3 is transmitted to a loudspeaker or earpiece 6, as applicable, which outputs an acoustic signal. If necessary, this sound is transmitted through a sound tube, which is fixed into the auditory canal using an otoplastic, to the eardrum of the hearing aid wearer. The power supply for the hearing aid, and in particular that for the signal processing unit 3 is effected by a battery 5 which is also integrated into the hearing aid housing 1.

Hearing impairments can be very diverse in their character. A hearing aid must compensate for the hearing impairment concerned. Hearing aids thus have numerous adjustment options. Any particular hearing aid must be individually tuned for the wearer of the hearing aid in a tuning procedure which is generally time-consuming.

In order to ensure that useful signals such as speech or music are made audible again by tuning of the hearing aid, a so called percentile analysis is used. With this percentile analysis, the transmission characteristics of the hearing aid are more precisely analyzed. In particular, the transmission characteristics of the hearing aid are represented as percentiles (percentage ranks). By this means, it is possible to determine frequency responses, for example, for loud and soft noise levels.

However, this method of measurement using percentiles has the disadvantage that a measurement takes a relatively long time, as a rule more than 30 seconds. This is disadvantageous, particularly in the case of in-situ tuning of hearing aids, because it is often necessary to make many measurements before the desired setting has been reached. For the wearer of the hearing aid this is very uncomfortable.

After a percentile analysis, the acoustician may determine, for example, that at high frequencies the amplification should be increased for low input levels. He will now manually change the compression break point, and the amplification in this region, but will not generally achieve the desired change optimally in the first step. One reason for this is that the hearing aid has a complex, non-linear characteristic, and another is that the hearing aid only offers limited adjustment possibilities. The acoustician will thus carry out several measurements iteratively, and possibly break off before the optimal setting has been reached, because the hearing aid wearer has only limited patience.

So, until now the wearer of a hearing aid has had to accept this prolonged tuning procedure, or the optimization would not be fully completed. As an alternative to this, until now use has also been made of measurement methods which are rapid but not suitable for everyday use, which increases the risk of poor tuning.

BRIEF SUMMARY OF THE INVENTION

The objective of the present invention is thus to be able to achieve high quality tuning in a shorter time.

In accordance with the invention, this objective is achieved by a method for tuning a hearing device by carrying out a percentile analysis to obtain at least one frequency response for the hearing device, determining a deviation of the frequency response from a target characteristic curve for the amplification, changing a setting of the hearing device so that the deviation is reduced, then determining an updated frequency response following the changes to the setting by presenting a constant noise signal or a single sinusoidal sweep at the input to the hearing device and measuring the level at the output.

In addition to this, inventive provision is made of a tuning device for tuning a hearing device, incorporating an analysis device for carrying out a percentile analysis for the purpose of obtaining at least one frequency response for the hearing device, a computing device for determining a deviation of the frequency response from a target amplification characteristic curve, an adjustment device for changing a setting of the hearing device so that the deviation is reduced, and a measurement device, which is independent of the analysis device, for determining an updated frequency response after any change to the settings, by the presentation of a constant noise signal or a single sinusoidal sweep at the input to the hearing device and measurement of the level at the output.

Advantageously, the tuning of the hearing device, and in particular of the hearing aid, is effected by a two-stage procedure, the steps of which are independent of each other. In the first step, an absolute measurement of the transmission characteristics of the hearing device is made by a percentile analysis. In a subsequent second step, a deviation from a target amplification characteristic curve is determined, the settings of the hearing device are changed and finally an updated frequency response or its change, as appropriate, is determined using a simple frequency response measurement (with no percentile analysis). So, using the percentile analysis a very precise starting basis is produced, whereas with the simple frequency response measurement it is possible very rapidly to check the effect of the changes to the settings. Overall, it is possible in this way to speed up the tuning procedure significantly.

It is advantageous if, before the step to make the changes, the up-to-date frequency response is determined in the same way as after the changes, and from this is determined a relative change in the frequency response due to the changes. By this means, the optimization phase is effected on the basis of relative changes, using fast measurements of the frequency response with no percentile analysis.

At the end of the tuning phase, a percentile analysis can be carried out once again. Using this optional analysis, it is possible to ensure that the tuning target has been optimally achieved.

In a form of embodiment which is also preferred, the steps to determine the deviation, to change the settings and to determine the updated frequency response are carried out automatically. Alternatively, of course, they can also be carried out manually or semi-automatically. However, automatic performance brings the advantage that the entire tuning procedure can be further speeded up.

In one special form of embodiment, in the determination of the deviation of the frequency response from a target amplification characteristic curve, the sum of the squared errors along an estimated gradient is minimized. In this way it is possible to reduce the deviation efficiently and selectively.

The settings of the hearing device, which are changed during the tuning, can relate to the amplification. The hearing device then automatically alters its amplification for the tuning procedure, or it is manually changed by an acoustician.

However, the settings for the hearing device may also related to compression. Both by changes to the amplification and also by changes to the compression it is possible to achieve the effect that the hearing device supplies sound which lies within the individual hearing range (below the threshold of discomfort and above the inaudible threshold) of the user of the hearing device.

The present invention will now be explained in more detail by reference to the attached drawings, in which are shown:

DESCRIPTION OF THE INVENTION

The exemplary embodiments which are described in more detail below represent preferred forms of embodiment of the present invention.

The invention is based on the thinking that the number of percentile measurements is reduced to one or two, and that the intermediate steps necessary for the purpose of realizing the desired change are carried out using a fast measurement (conventional frequency response measurement using a short noise signal or sinusoidal sweep). If necessary, the performance of the intermediate steps using the fast measurement can be automated.

Figure 1:
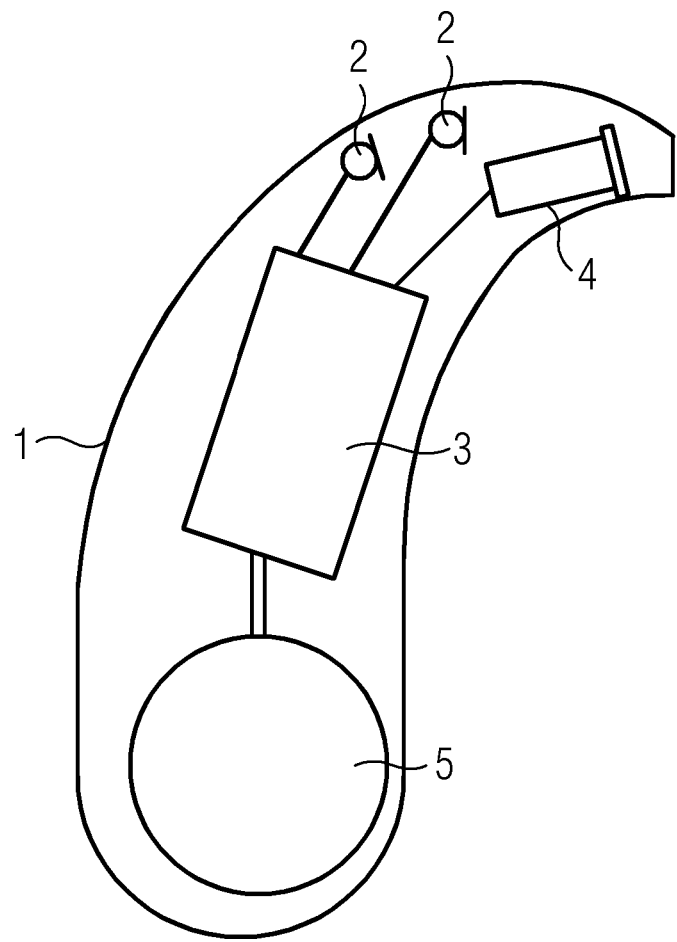
FIG. 1 the principle of the structure of a hearing aid in accordance with the prior art.
Figure 2:
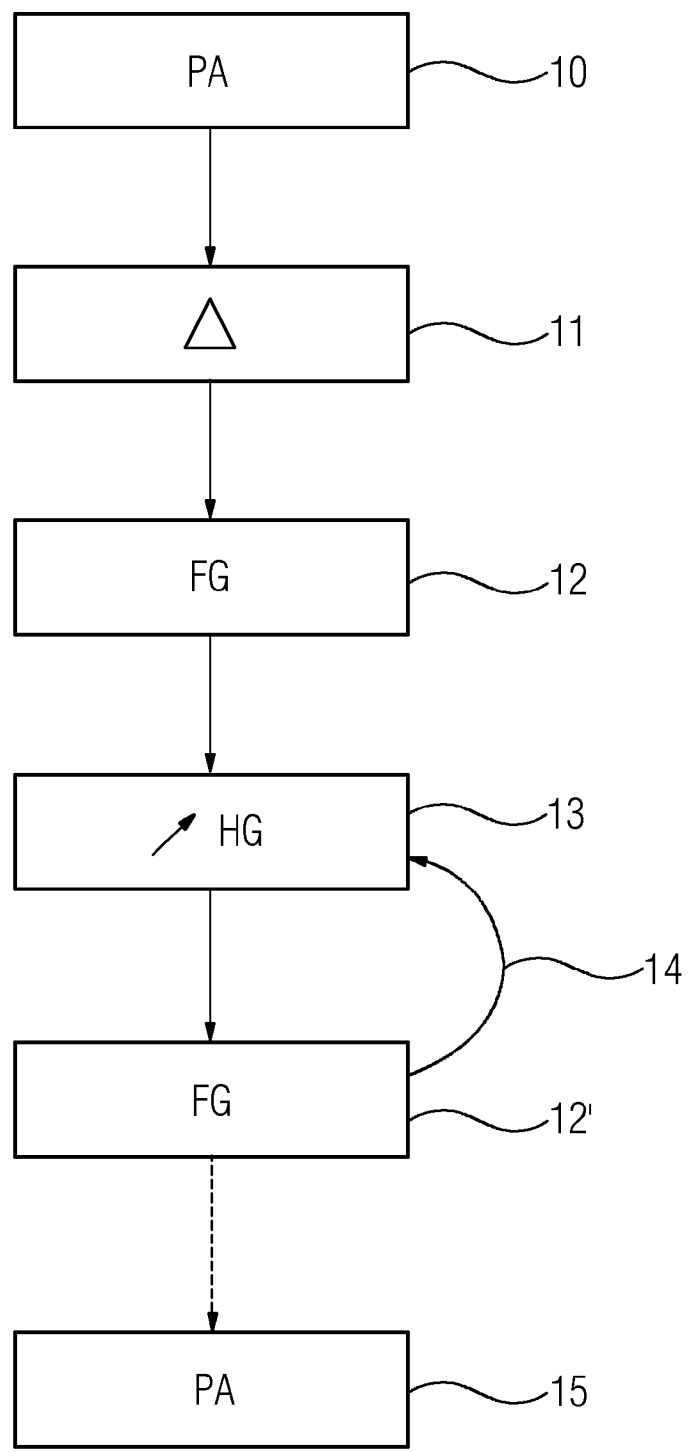
FIG. 2 a flow diagram for the inventive method.

The principle of the inventive tuning procedure, in which the transmission characteristics of a hearing device, and in particular a hearing aid, are to be individually tuned for a user, can be explained graphically by the specific example in FIG. 2. To start, a percentile analysis 10 of the hearing device is undertaken. By this, a set of amplification characteristic curves is obtained for the hearing aid. In particular, the frequency response of the hearing device for soft and loud noise levels is thereby obtained. The percentile analysis represents a very precise absolute measurement. Following this, there is a determination 11 of the deviation of the amplification characteristic curve, obtained by the percentile analysis 10, from a target amplification characteristic curve. For example the target amplification characteristic curve can be prescribed by the experience of the acoustician, but it can also be obtained from a audiogram by a tuning formula (e.g. NAL NL1).

At this point, the frequency response of the hearing aid is measured by a first frequency response measurement 12 on the basis solely of a short noise signal or a sinusoidal sweep. This measurement represents the reference for a later second frequency response measurement 12'.

In a step which then follows, a change 13 is made to the settings of the hearing aid or the hearing device. This setting or readjustment of the hearing aid can be effected automatically on the basis of the deviation from the target amplification characteristic curve, or manually (by the input of changes, desired by the acoustician, for each frequency and level).

In a step which follows, the second frequency response measurement 12' is made, where the first and second frequency response measurements 12, 12' are each significantly faster than the percentile analysis 10. As in the case of the first frequency response measurement 12, the second frequency response measurement 12' is a conventional measurement of the transmission function of the hearing aid by which, for example, a short noise signal or a sinusoidal sweep (chirp signal) is applied at the input to the hearing aid. The corresponding output level is then measured at the output from the hearing aid. A frequency response measurement of this type can be realized in a few seconds (commonly 2 to 3 seconds).

Using the two frequency response measurements 12, 12' it is possible to determine the relative shift in the frequency response, which is evoked by the changing 13 of the settings. Using the relative shift and the absolute measurement from the percentile analysis it is possible to deduce the up-to-date frequency response.

If, after the second frequency response measurement 12', it is determined by reference to the updated frequency response that the tuning objective has not yet been reached, a change 13 can again be made to the hearing aid settings, either automatically or manually. Since the only change is again to the settings it is again possible, for the purpose of checking the adjustment which now applies, to use the fast measurement 12 of the frequency response, because the same errors arise in the measurement before the new change to the hearing aid settings and after it, and these therefore cancel each other out because of the differential approach. Thus, for example, there is a distortion of the signal in the hearing aid due to the removal of interference noise if the frequency response measurement is effected using a noise signal at the input. However, if the same measurement using the noise signal at the input is made after a change in the settings of the hearing aid, there is the same distortion, and the distortions cancel each other out with the relative approach. The same applies, for example, with a distortion due to feedback suppression when the measurement is made using a sinusoidal tone (sinusoidal sweep). In addition, distortions can also arise, for example, because of the transient response of the hearing aid. But these too are rendered imperceptible by the differential approach.

In order to be able to use the relative measurements, frequency response measurements 12 or 12' must be made respectively before and after a change 13 to the settings of the hearing aid. The arrow 14 in FIG. 2 indicates that the changing 13 of the hearing aid settings and the frequency response measurement 12' can be repeated any desired number of times in order ultimately to achieve optimal tuning. In each case, the preceding frequency response measurement serves as the reference for the relative shift in the frequency response concerned.

So, the sequence 12', 13 will preferably be repeated several times automatically, and the hearing aid settings optimized as appropriate for the residual deviations. In doing this, use can also be made of an optimization method which minimizes the sum of the squared errors across a gradient estimate. At the end, a second percentile measurement 15 can optionally be carried out for the purpose of verifying the settings.

Figure 3:
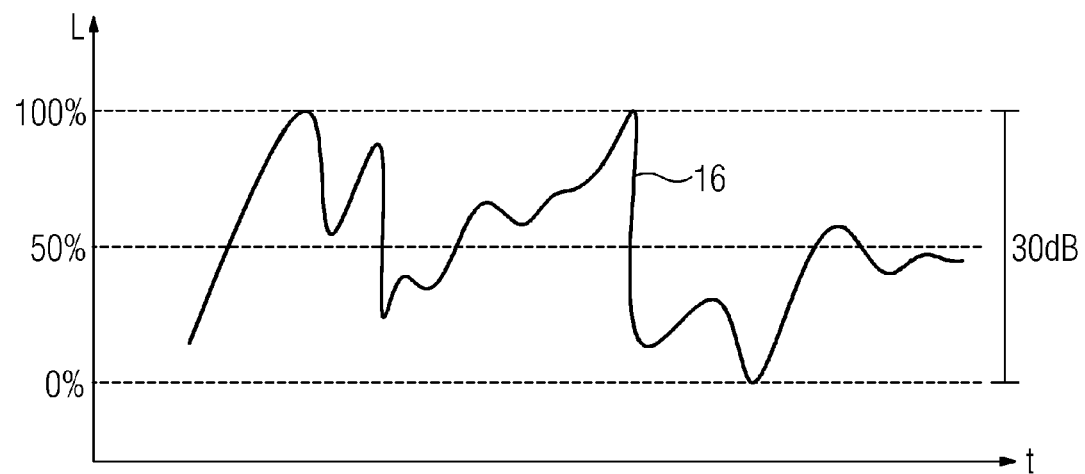
FIG. 3 a percentile analysis of a signal and
FIG. 4 the compression of a sound into the hearing range of a listener.
Figure 4:
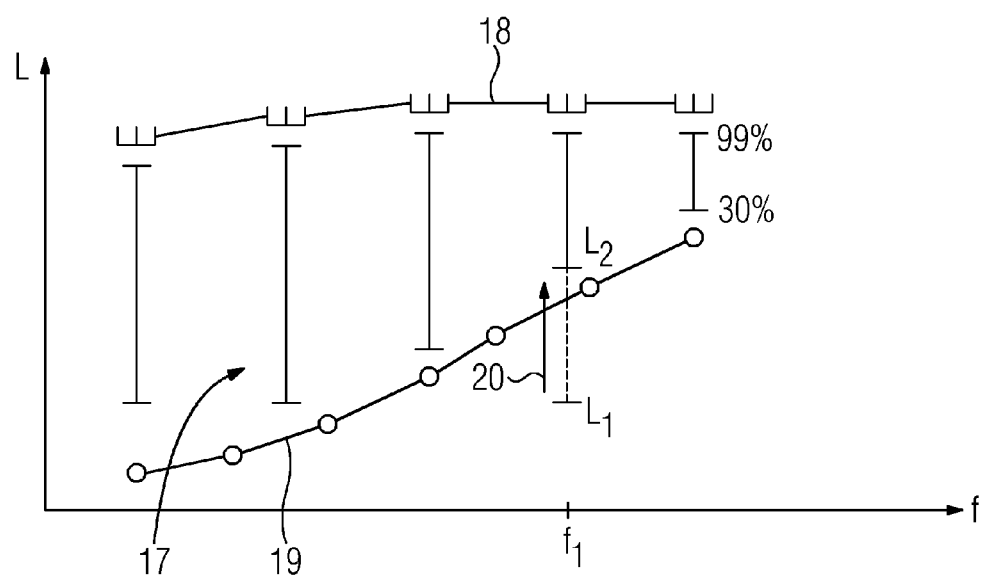

Referring to FIGS. 3 and 4, details of the inventive tuning procedure can be explained visually. FIG. 3 shows a section of a percentile analysis, for example of a voice signal in a frequency channel of the hearing aid. The signal in this frequency channel has, for example, a dynamic range of 30 dB. The points of intersection of the graph of the signal level 16 with the horizontal 50% line specify how often sound is presented which has a relative level of 50% (50% percentile). Of especial significance for acoustics are the 99% percentile and the 30% percentile.

The objective is, for example, to bring the 99% percentile and the 30% percentile into the audible range 17 for the wearer of the hearing aid. This audible range 17 is located between the threshold of discomfort 18 and the inaudible threshold 19. In the present example, the 30% and 99% percentiles for all frequencies except the frequency $f_1$ lie within the audible range 17. According to the percentile analysis, the 30% percentile for a level $L_1$ is located below the inaudible threshold 19. Hence the amplification in the hearing aid must be increased for the frequency $f_1$, or for the corresponding frequency channel, as applicable. This increase is indicated symbolically in FIG. 4 by the arrow 20. By changing the amplification setting, the 30% percentile ends up at level $L_2$. This change in the amplification can be effected in one step, or even in several individual steps, and can be determined as a relative magnitude by simple frequency response measurements 12, 12'. The 30% percentile then finally lies on a target amplification curve within the audible range.

A tuning device for carrying out the tuning procedure will, for example, have an analysis device with which the percentile analysis can be carried out. In addition, it will have a computing device to determine the deviation of the frequency response, obtained from the percentile analysis, from a target amplification characteristic curve. Further, an adjustment device will be provided to enable the settings of the hearing device or hearing aid, as applicable, to be changed in particular in such a way that the deviation from the target amplification is reduced. Finally, the tuning device will incorporate a measurement device, which is independent of the analysis device, to determine the up-to-date frequency response after a change to the settings, whereby a constant noise signal or a single sinusoidal sweep is presented at the input to the hearing aid and the output level from the hearing aid is measured.

The inventive method thus enables hearing aids to be tuned in an advantageous way, by means of high-quality percentile analysis, where however the overall tuning procedure is significantly speeded up by simple measurement(s) of the frequency response. Using this multi-stage procedure with different algorithms it is possible very rapidly to find an optimal setting for a hearing aid.

The invention claimed is:

1. A method for adjusting a hearing apparatus, the method which comprises:
    performing a percentile analysis for obtaining at least one frequency response for the hearing apparatus;
    determining a deviation of the frequency response from a target amplification characteristic curve;
    determining an up-to-date frequency response by presenting a constant noise signal or a single sinusoidal sweep at an input to the hearing apparatus and measuring a level thereof at an output of the hearing apparatus;
    subsequently changing settings for the hearing apparatus in order to reduce the deviation of the frequency response from the target amplification characteristic curve;
    subsequently determining the up-to-date frequency response with the changed settings by presenting the constant noise signal or the single sinusoidal sweep at the input to the hearing apparatus and measuring a level thereof at the output of the hearing apparatus, and determining a relative change in the frequency response due to the changes in the settings; and
    performing a further percentile analysis following the step of determining the relative change.

2. The method according to claim 1, which comprises performing the steps of determining the deviation, changing the settings, and determining the up-to-date frequency response automatically.

3. The method according to claim 1, wherein the step of determining the deviation includes minimizing a sum of squared errors by way of a gradient estimation.

4. The method according to claim 1, wherein the settings of the hearing apparatus to be adjusted are amplification settings.

5. The method according to claim 1, wherein the settings of the hearing apparatus to be adjusted are compression settings.

6. An adjusting device for adjusting a hearing apparatus, the adjusting device comprising:
    an analysis device for obtaining at least one frequency response for the hearing apparatus, said analysis device being configured for carrying out a percentile analysis for obtaining the at least one frequency response;
    a computing device for determining the deviation of the frequency response from a target amplification characteristic curve;
    an adjustment device for changing settings of the hearing apparatus in order to reduce the deviation; and
    a measurement device independent of said analysis device, for determining an up-to-date frequency response, after the changing of the settings, by presenting at an input of the hearing apparatus a constant noise signal or a single sinusoidal sweep and measuring a level thereof at an output of the hearing apparatus;
    said measurement device being configured for determining the up-to-date frequency response before said adjustment device changes the settings of the hearing apparatus and, in the same way, after said adjustment device changes the settings, and for determining therefrom a relative change in the frequency response due to the changes in the settings; and
    said analysis device being configured for carrying out a further percentile analysis following the step of determining the relative change.

7. A method for adjusting a hearing apparatus, the method which comprises:
    performing a percentile analysis for obtaining at least one frequency response for the hearing apparatus;

determining a deviation of the frequency response from a target amplification characteristic curve including minimizing a sum of squared errors by way of a gradient estimation;

determining an up-to-date frequency response by presenting a constant noise signal or a single sinusoidal sweep at an input to the hearing apparatus and measuring a level thereof at an output of the hearing apparatus;

subsequently changing settings for the hearing apparatus in order to reduce the deviation of the frequency response from the target amplification characteristic curve;

subsequently determining the up-to-date frequency response with the changed settings by presenting the constant noise signal or the single sinusoidal sweep at the input to the hearing apparatus and measuring a level thereof at the output of the hearing apparatus, and determining a relative change in the frequency response due to the changes in the settings.

8. The method according to claim 7, which comprises performing the steps of determining the deviation, changing the settings, and determining the up-to-date frequency response automatically.

9. The method according to claim 7, wherein the settings of the hearing apparatus to be adjusted are amplification settings.

10. The method according to claim 7, wherein the settings of the hearing apparatus to be adjusted are compression settings.

11. An adjusting device for adjusting a hearing apparatus, the adjusting device comprising:

an analysis device for obtaining at least one frequency response for the hearing apparatus, said analysis device being configured for carrying out a percentile analysis for obtaining the at least one frequency response;

a computing device for determining the deviation of the frequency response from a target amplification characteristic curve, including minimizing a sum of squared errors by way of a gradient estimation;

an adjustment device for changing settings of the hearing apparatus in order to reduce the deviation; and a measurement device independent of said analysis device, for determining an up-to-date frequency response, after the changing of the settings, by presenting at an input of the hearing apparatus a constant noise signal or a single sinusoidal sweep and measuring a level thereof at an output of the hearing apparatus;

said measurement device being configured for determining the up-to-date frequency response before said adjustment device changes the settings of the hearing apparatus and, in the same way, after said adjustment device changes the settings, and for determining therefrom a relative change in the frequency response due to the changes in the settings.

* * * * *